United States Patent [19]

Scortichini et al.

[11] Patent Number: 5,230,783
[45] Date of Patent: Jul. 27, 1993

[54] ELECTROLYTIC CELL AND PROCESS FOR THE LABELING OF PROTEINS AND PEPTIDES

[75] Inventors: Carey L. Scortichini, Sanford; Janeth M. Bartlett, Midland, both of Mich.

[73] Assignee: The Dow Chemical Company, Midland, Mich.

[21] Appl. No.: 701,438

[22] Filed: May 15, 1991

[51] Int. Cl.$^5$ ............................................. G01N 27/26
[52] U.S. Cl. ................................. 204/153.12; 204/412; 204/415; 204/153.1; 204/153.13
[58] Field of Search ................... 204/153.13, 153.12, 204/153.1, 415, 412

[56] References Cited

U.S. PATENT DOCUMENTS

| | | | |
|---|---|---|---|
| 3,441,490 | 4/1969 | Johansson | 204/412 |
| 3,833,490 | 9/1974 | Bizot et al. | |
| 4,184,937 | 1/1980 | Tataria et al. | 204/412 |
| 4,233,121 | 11/1980 | Gyori et al. | |
| 4,389,290 | 6/1988 | Gratzel et al. | |
| 4,464,236 | 8/1984 | Noding | |
| 4,644,237 | 2/1987 | Druy et al. | |
| 4,666,570 | 5/1987 | Matsuoka et al. | |
| 4,849,215 | 7/1989 | Gottardi | |
| 4,859,305 | 8/1989 | Scheider et al. | 204/412 |
| 5,126,034 | 6/1992 | Carter et al. | 204/403 |

FOREIGN PATENT DOCUMENTS

| | | |
|---|---|---|
| 0135638 | 6/1988 | European Pat. Off. |
| 1187308 | 9/1970 | Fed. Rep. of Germany |
| 2920562 | 12/1979 | Fed. Rep. of Germany |
| 1106786 | 5/1986 | Japan |
| 1257490 | 11/1986 | Japan |
| 7302221 | 8/1978 | Netherlands |
| 0535271 | 12/1976 | U.S.S.R. |
| 0517222 | 8/1977 | U.S.S.R. |
| 0597744 | 3/1978 | U.S.S.R. |
| 0601925 | 7/1979 | U.S.S.R. |

OTHER PUBLICATIONS

Wong et al., Chemical Abstracts, vol. 90, No. 1, Jan. 1, 1979, abstract No. 1882.

Teare et al., Chemical Abstracts, vol. 90, No. 7, Feb. 17, 1979, abstract No. 50635.

Rzendowska et al., Chemical Abstracts, vol. 70, No. 7, Feb. 17, 1969, abstract No. 26249.

Fittkau et al., Chemical Abstracts, vol. 72, No. 19, May 11, 1970, abstract No. 96751.

Khalkhali et al., Chemical Abstracts, vol. 71, No. 25, Dec. 22, 1969, abstract No. 119694.

DeWulf et al., J. Electrochem. Soc., vol. 135, pp. 1977-1985 (1988), entitled "Application of Nafion-Platinum Electrodes (Solid Polymer Electrolyte Structures) to Voltammetric Investigations of Highly Resistive Solutions".

(List continued on next page.)

Primary Examiner—John Niebling
Assistant Examiner—Bruce F. Bell
Attorney, Agent, or Firm—Karen L. Kimble

[57] ABSTRACT

An electrolytic cell for the labeling of proteins, peptides and other organic molecules employs a cathodic half cell and an anodic half cell, where a porous working electrode is located in one half cell and a counter electrode is located in the other of the half cell, the two half cells being divided by a separator. A reference electrode located in the half cell containing the working electrode, and placed outside the current path between the working electrode and the counter electrode confers precise control of the working electrode potential, which allows the maximum rate of labeling to be achieved while minimizing oxidative damage to the protein, peptide or organic molecules. Saturation of the working electrode with non-radioactive label coupled with a ratio of working electrode surface area to volume of half cell containing the working electrode between 0.001 cm$^{-1}$ to about 10 cm$^{-1}$ minimizes the problem of loss of activity of radiolabel due to adsorption on the working electrode.

21 Claims, 4 Drawing Sheets

OTHER PUBLICATIONS

Goodridge et al., "The Design of Laboratory Cells", *Technique of Electroorganic Synthesis, Part I*, ed. N. L. Weinberg, New York, pp. 80–81 (1974).

Wong et al., *Nucl. Med. Biol.* vol. 15, No. 5, pp. 505–509 (1988), entitled "Comparison of the Iodogen and the Microelectrochemical Techniques for the Radioiodination of Monoclonal Antibody 140.240".

Rosa et al., *Biochim. Biophys. Acta,* vol. 86, pp. 519–526 (1964), entitled "Labeling of Human Fibrinogen with $^{131}$I by Electrolytic Iodination".

Katayama-Aramata et al., *Electrochimica Acta,* vol. 28, No. 6, pp. 777–780 (1983), entitled "Metal Electrodes Bonded on Solid Polymer Electrolyte Membranes (SPE)-The Behavior of Platinum Bonded on SPE for Hydrogen and Oxygen Electrode Processes".

Raoult et al., *J. App. Electrochemistry,* vol. 15, pp. 85–91 (1985), entitled "Use of Ion Exchange Membranes in Preparative Organic Electrochemistry.II. Anodic Dimethoxylation of Furan".

Rosa et al., *Biochim. Biophys. Acta,* vol. 133, pp. 486–498 (1967) entitled "Chemical and Biological Effects of Iodination on Human Albumin".

Russell, *Int. J. Appl. Radiat. Isot.,* vol. 28, pp. 241–249 (1977), entitled "Carrier Electrochemistry of Pertechnetate: Application to Radiopharmaceutical Labeling by Controlled Potential Electrolysis at Chemically Inert Electrodes".

Benjamin, *Int. J. Appl. Radiat. Isot.,* vol. 20, pp. 187–194 (1969) entitled "A Rapid and Efficient Method of Preparing $^{99m}$Tc-Human Serum Albumin: Its Clinical Applications".

Benjamin et al., *J. Nucl. Med.* vol. 11, pp. 147–154 (1970), entitled "Electrolytic Complexation of $^{99m}$Tc at Constant Current: Its Applications in Nuclear Medicine".

Dworkin et al., *J. Nucl. Med.,* vol. 12, pp. 562–565 (1971), entitled "Rapid Closed-System Production of $^{99m}$Tc-albumin using electrolysis".

Dixit et al., *Electrochemical Acta,* vol. 27, No. 5, pp. 561–563 (1981), entitled "Electrochemical Synthesis of Benzyl Benzoate at Carbon Anode".

Stanko, et al., Otkrytiya, Izobret., Prom. Obraztsy, Tovarnye Znaki, 53 (1976) 151 (SU 421254).

Stanko, et al., Isotopenpraxis, 9 (1973) 260-4.

Fittkau, et al., Wiss. Z. Karl-Marx-Univ. Leipzing, Math.-Naturwiss. Reihe, 18 (1969) 551-7.

Kulakov, et al., Vopr. Med. Khim., 31 (1985) 98-100.

Aldonyasov, et al., Isotopenpraxis, 9 (1973) 55-9.

Pierce Product Literature Regarding Various Iodination Reagents.

ELECTROLYTIC CELL AND PROCESS FOR THE LABELING OF PROTEINS AND PEPTIDES

BACKGROUND OF THE INVENTION

1. Field of the Invention

This invention relates to an electrolytic cell and a process for utilizing the electrolytic cell to achieve the labeling of proteins, peptides and other organic molecules. More particularly, this invention relates to an electrolytic cell and a process for utilizing the electrolytic cell to achieve the radiolabeling of proteins, peptides and other organic molecules.

2. Description of Related Art

Present techniques for labeling proteins, peptides and other organic molecules with halogens or other labels suffer from several drawbacks. Chemical labeling processes, for example, often are difficult to scale-up and tend to damage the proteins and peptides which are to be labeled. In addition, because these same chemical labeling processes may have low yields, unreacted label has to be separated from the labeled material. While this purification step not only makes chemical labeling processes less efficient, in the case of radioactive labels it exposes the operator to a hazardous substance. Among the current processes for radiolabeling proteins is solid phase iodination which employs oxidative techniques for producing an electrophilic iodine species (I+) from sodium iodide.

Present electrochemical techniques for labeling proteins, peptides and other organic molecules with halogens or other labels, such as technetium and rhenium, suffer from other drawbacks. For example, electrochemical labeling processes often use platinum or gold as the anode and cathode of the electrolytic cell. Using current electrochemical techniques, biological materials can be iodinated on a microgram scale with up to 80% incorporation of radioiodine. In order to get short reaction times, many workers use a relatively high ratio of anode surface area to electrolyte volume. This high ratio of anode surface area to electrolyte volume is commonly accomplished by using a platinum crucible which functions as the reaction vessel as well as the anode. Platinum crucibles, however, are inadequate for commercial operation for a number of reasons. For example, platinum crucibles are not practical because their geometry precludes maintaining a uniform potential across the anode surface, particularly in solutions of low conductivity. Also, their geometry does not allow easy variation of the surface area/electrolyte volume ratio. This is due to the fact that, for any shape, area does not increase as fast as volume. Further, these crucibles use relatively large amounts of platinum or gold which must be either thrown away after each use or subjected to cumbersome cleaning procedures which generate liquid radioactive waste.

Present electrochemical techniques also suffer from drawbacks similar to chemical techniques. For example, in the context of the commercial production of radiolabeled monoclonal antibodies (MAbs), the anodes, cathodes, membranes, and other components of the electrolytic cell can become contaminated with the radioactive labeling agent. The cost of radioactive waste disposal makes it necessary to pay more attention to the efficiency of use of the isotope and to where it ends up when efficiency is less than 100%.

SUMMARY OF THE INVENTION

The present invention provides an electrochemical cell for use in an improved process for the labeling of proteins, peptides and other organic molecules, particularly monoclonal antibodies with halogens or other labels, such as technetium and rhenium. It is intended that the term "label" as used herein include labels which can be either radioactive or non-radioactive. The cell employs a cathodic half cell containing a catholyte and an anodic half cell containing an anolyte divided by a separator which assists in preventing the gross mixing of the anolyte and catholyte while permitting the flow of ionic current. Labeling of the proteins, peptides and other organic molecules may occur in either half cell at a working electrode. When the label is oxidized to become a labeling agent, a porous anode placed within the anodic half cell serves as the working electrode and a cathode placed within the cathodic half cell serves as the non-working or counter electrode. When the label is reduced to become a labeling agent, a porous cathode placed within the cathodic half cell serves as the working electrode and an anode placed within the anodic half cell serves as the non-working electrode. A reference electrode placed outside the current path between the working electrode and the nonworking confers precise control of the working electrode potential, which allows the maximum rate of labeling to be achieved while minimizing oxidative damage to the protein, peptide or organic molecules.

The cell confers many advantages which result in very high yields of labelled product, easier scale-up of the process, and, in the case of radiolabeling, reduced volume of liquid radioactive waste.

DETAILED DESCRIPTION OF THE INVENTION

Figure 1:
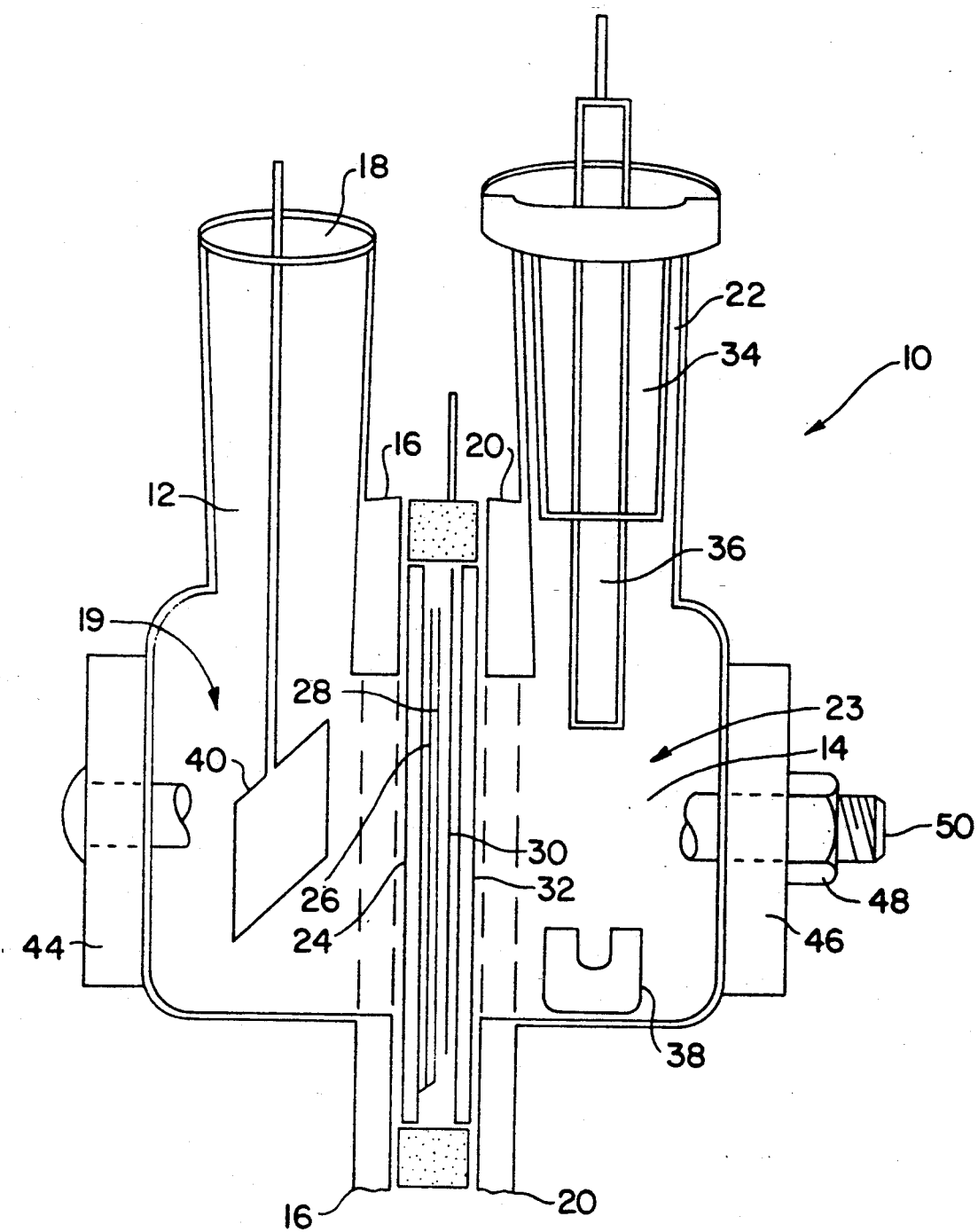
FIG. 1 shows a schematic diagram of the electrolytic cell of the present invention.
Figure 3:
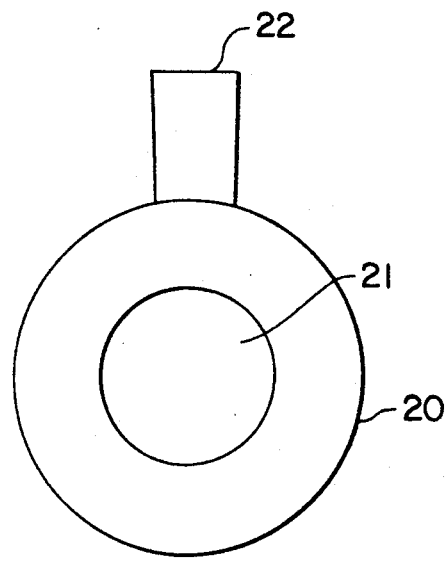
FIG. 3 shows a front elevational view of the glass half cell.
Figure 2:
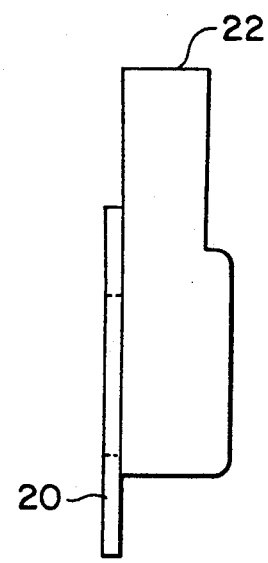
FIG. 2 shows a side view of a glass half cell.
Figure 6:
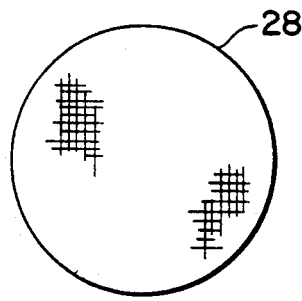
FIG. 6 shows a front elevational view of a porous anode.
Figure 5:
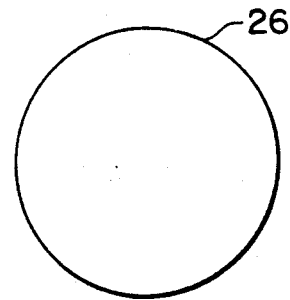
FIG. 5 shows a front elevational view of a separator.
Figure 4:
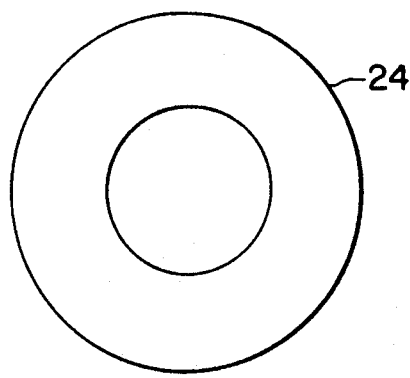
FIG. 4 shows a front elevational view of a rubber gasket.
Figure 7:
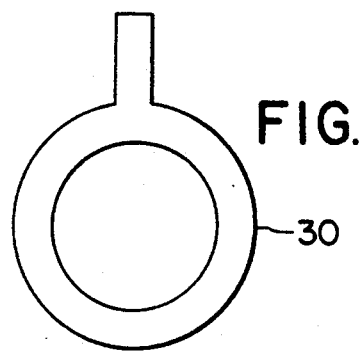
FIG. 7 shows a front elevational view of a metal ring contact.

In the preferred embodiment, cell 10 consists of two identical glass halves, a first glass cathodic half cell 12 and a second glass anodic half cell 14 (FIGS. 1, 2 & 3). First glass half 12 has an annular ring 16 with a ground glass face, said ring 16 circumscribing an opening 17 (not shown), an open top 18, and a reaction chamber 19 while second glass half 14 has an annular ring 20 with a ground glass face, said ring 20 circumscribing an opening 21, an open top 22, and a reaction chamber 23. Squeezed between ring 16 and ring 20 are a first rubber gasket 24 (FIGS. 1 & 4), a separator 26 (FIGS. 1 & 5), a porous anode 28 (FIGS. 1 & 6), a metal ring contact 30 (FIGS. 1 & 7), and a second rubber gasket 32. The relative size of the various pieces is shown in FIGS. 2 through 11. As can be seen, the inside diameter of the rubber gaskets 24 and 32 determines the active area of the anode 28.

A thermometer adapter 34 holding a silver/silver chloride reference electrode 36 is removably fitted into glass half 14 (FIG. 1). Glass half 12, on the other hand, is fitted with a platinum or gold foil, or stainless steel cathode 40. While FIG. 1 shows glass half 14 having a magnetic stir bar 38 located therein, glass half 12 is also of sufficient size to contain a similar magnetic stir bar. Chambers 19 and 23 are designed to allow closer placement of the bottom of their respective glass halves 12 and 14 to a magnetic stir plate so that the stirring provided by a magnetic stir bar would be more reliable.

Figure 8:
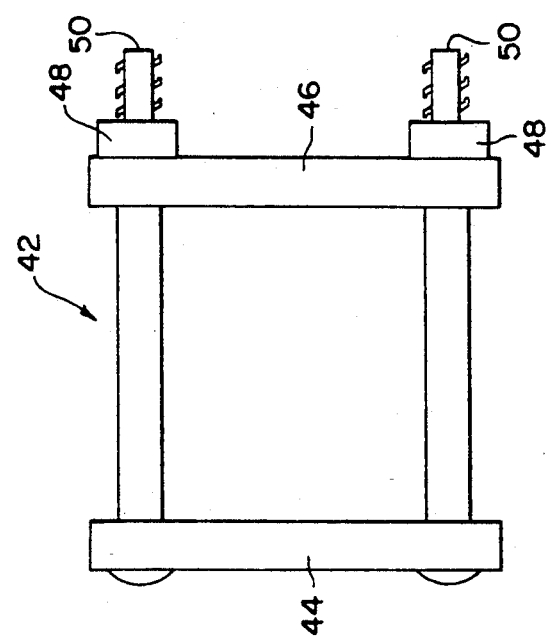
FIG. 8 shows a plan view of a clamp.
Figure 10:
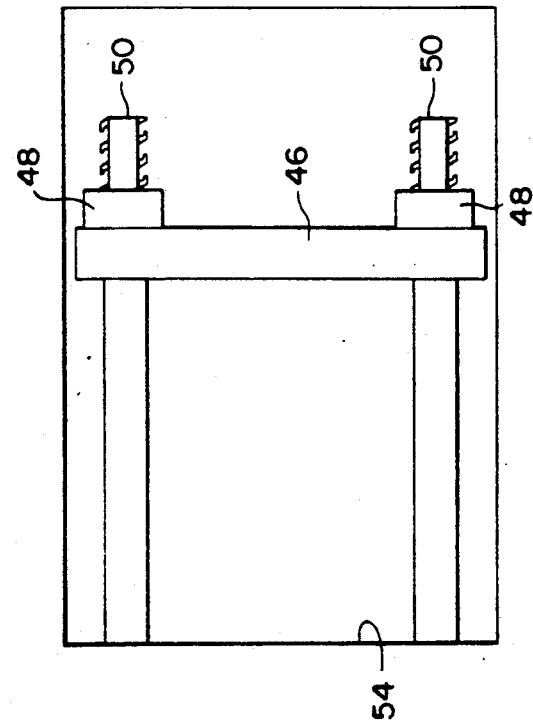
FIG. 10 shows a plan view of a combined clamp and heat sink.
Figure 9:
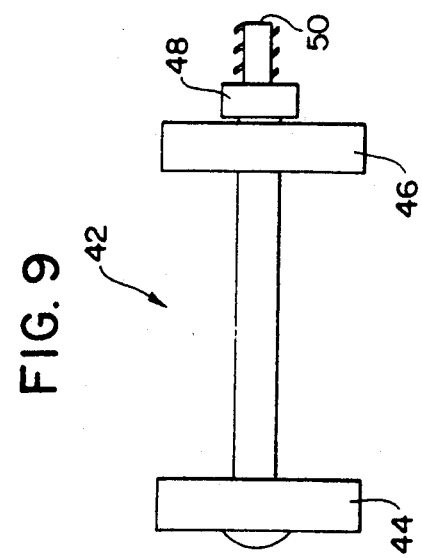
FIG. 9 shows a side view of the clamp of FIG. 8.
Figure 11:
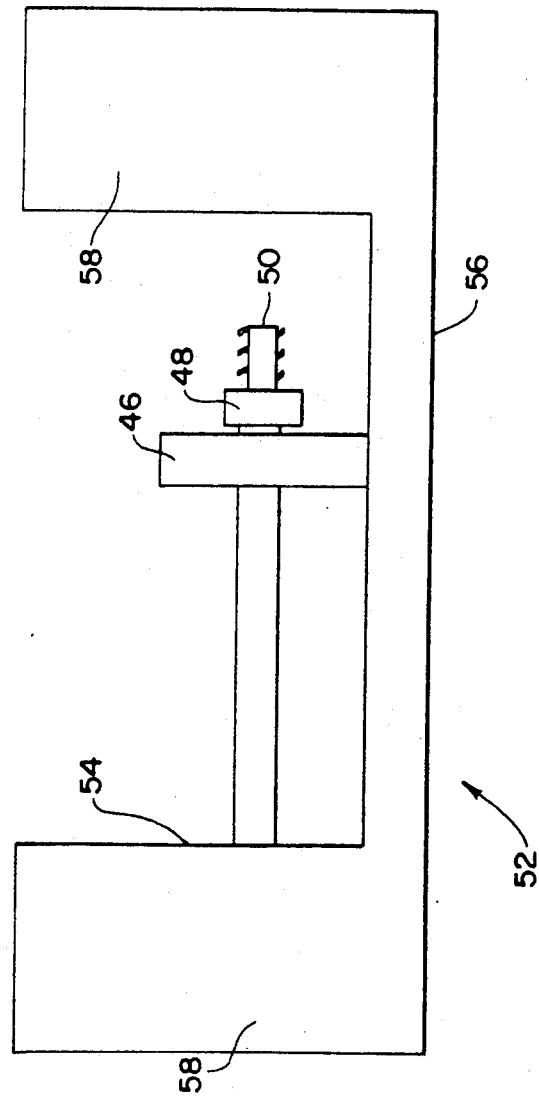
FIG. 11 shows a side view of the combined clamp and heat sink of FIG. 10.

While half cell 12 and half cell 14 may be held together in a variety of ways, a clamp 42 applied on the two ends of the cells, rather than ring 16 and ring 20, provides for more even pressure without the need for any sealant or adhesive (FIGS. 8 & 9). The clamp 42 shown in FIGS. 8 & 9 consists of a fixed bar 44 and a movable bar 46 where the movable bar 46 is operable by tightening or loosening nuts 48 on a pair of threaded rods 50. Fixed bar 44 and movable bar 46 are shaped to match the backside configuration of half cells 12 and 14. Preferably, both the respective bars and the respective backsides of the half cells are flat for even pressure distribution and good contact. The clamp 42 could also be an integral part of a metal block 52 that could serve as a heat sink (FIGS. 10 & 11). The block 52 shown in FIGS. 10 & 11 consists of a movable bar 46 and an end 54 which acts as and replaces fixed bar 42. The block 52 also has a base 56 and an upstanding wall 58 (of which end 54 is a part) which surrounds cell 10 and serves as a support for the cell 10. The temperature of the block 52 could be maintained in any number of ways, including placing it in an incubator or circulating a fluid through a channel in the block 52.

While the cell 10 described above is constructed of glass, it may be constructed of any of a wide variety of materials, including various plastics such as polypropylene, polycarbonate, Teflon, and Lucite, or any combination of the materials. The general requirements are that the materials of construction be compatible with the process chemicals under the conditions employed, maintaining their structural integrity and not adding undesirable materials to the product.

Radioactive and non-radioactive halogens can be used for the labeling of proteins, peptides and other organic molecules, particularly monoclonal antibodies. Among the other labels contemplated for use in the present invention are technetium and rhenium. These labels also can be either radioactive or non-radioactive.

In the cell 10 described above, the porous anode 28 serves as the working electrode. The porous anode 28 is made from a metal selected from the group consisting of gold, platinum and a mixture of 90% platinum/10% rhodium. It is postulated that gold may be a better anode material for iodinations where the protein, peptide or other organic molecule to be halogenated is very oxidation sensitive. In general, any electrically conducting or semiconducting material may be used as the anode. Examples of suitable materials include various forms of carbon, lead, lead dioxide, noble metals (Groups VIII and IB in the Periodic Chart) and their oxides (for example, platinum oxide), and noble metals or their oxides as coatings on a valve metal such as titanium. The anode material is chosen for its ability to effect the desired conversion efficiently and its resistance to corrosion. With respect to halogenations and radiohalogenations, the noble metals are advantageous due to their inertness and their ability to efficiently oxidize halides to active halogenating agents. Noble metal oxides, however, are not suitable for iodinations or radioiodinations due to the formation of iodate.

Where a porous cathode serves as the working electrode, any electrically conducting or semiconducting material may generally be used as the cathode 40. Examples of suitable materials include various forms of carbon, stainless steels, noble metals (Groups VIII and IB in the Periodic Chart) and their oxides (for example, platinum oxide), and transition metals such as copper and nickel.

While metal contact ring 30 is not a critical component of the cell 10 assembly, it does assure that an electrical contact is maintained with the working electrode. The metal contact ring 30 is especially useful when very thin pieces of expensive platinum or gold are used as the anode or cathode in the working electrode. In situations where these thin pieces of platinum or gold cannot withstand direct connection to a power source by an allegator clip, the metal contact ring 30 can serve as the contact point.

Whether a porous cathode or a porous anode serve as the working electrode, it is important that the edges of the working electrode be covered by the gaskets 24 and 32 so as to diminish mass transfer at the edges. Enhanced mass transfer to the edges makes it difficult to maintain a uniform potential across the working electrode which may cause problems with the labeling agent. For example, if the potential is not high enough, no active labeling agent will be produced from iodide, while if the potential is too high, iodide will be oxidized to iodate, which is not an active labeling agent. Where the edges of the working electrode are covered, the location of the reference electrode is not critical as long as it is placed outside the current path because the current cannot get around the edges of the working electrode. Where the edges of the working electrode are uncovered, however, it is more difficult to locate the reference electrode outside the current path.

The separator 26 assists in preventing the gross mixing of the anolyte and catholyte while permitting the flow of ionic current between anode and cathode. The separator 26, in general, should be electrically insulating, and may be made of a wide variety of materials, including, but not limited to, fritted glass, sintered glass powders, porous or foamed plastics such as Teflon, asbestos diaphragms, porous ceramic materials, ion exchange membranes and ultrafiltration membranes. In one aspect of the invention, separator 26 is a Nafion 117 cation exchange membrane. By being cationic, the separator 26 ensures that the radiohalides remain in the anode compartment of the present invention.

The present invention also contemplates utilizing an anion exchange membrane as the separator 26. In this embodiment, the radiohalide is added to the catholyte and the halide diffuses across the anion membrane separator 26 in response to a concentration gradient. The halide then encounters the porous metal layer 28 where, if the layer is at a suitable potential vs. the reference electrode 36, the halide is oxidized to an active halogenating agent and reacts with the protein material if the porous anode 28 is sufficiently porous. Presently available anion exchange membranes useful for this embodiment are the Raipore anion exchange membranes 1030, 4030 and 5030 (Pall RAI, Inc.).

An advantage of placing the radiohalide in the catholyte is that the problem of separating unreacted radioactive material from radiolabeled protein is diminished. This result is further enhanced by placing porous anode 28 directly adjacent separator 26. With such an arrangement, the radioiodide reacts with the protein at porous anode 28 as it enters anode half cell 14, and the cell is turned off when there is essentially no unreacted radioactive iodide left in anode half cell 14 which has to be separated from the radiolabeled protein. A disadvantage of placing the radiohalide in the catholyte is that much of the radiohalide remains in the separator 26. However, this may not be a disadvantage in a commercial application where repeated or continuous use may make the initial saturation of the separator 26 irrelevant.

Any supporting electrolyte can be used in the catholyte or anolyte. Examples of supporting electrolytes commonly used include sodium chloride, phosphate buffers, tetraalkylammonium salts and alkali metal acetates. Also, the cell 10 may be used without any supporting electrolyte in the working electrode compartment if this is desired for process reasons.

Regardless of the supporting electrolyte utilized, some form of stirring must be used in the half cell containing the working electrode to assure adequate mixing of reagents and contact with the working electrode. In the cell 10 described above, stir bar 38 provides the mixing. Other methods for providing mixing include sparging gas into the half cell. It is contemplated that stirring in both half cells would provide benefits when the labeling agent is located in one half cell and the material to be labeled is located in the other half cell.

In an embodiment of the present invention for halogenation of proteins where the anodic half cell 14 contains the working electrode, a different form of anode 28 and a superior arrangement of anode 28 and reference electrode 36 is used. A thin piece of porous anode 28 material used in the manner shown in FIG. 1 provides for more economical use of expensive precious metal anodes, increased economy and flexibility in cleaning procedures, and provides for precise control of the anode potential and hence the efficiency of the halogenation reaction. The placement of the reference electrode 36 outside the current path also confers precise control of the anode potential, which allows the maximum rate of halogenation to be achieved while minimizing oxidative damage to the protein. Placement of the reference electrode 36 outside the current path, however, makes it essential that the working electrode be porous. The reference electrode 36 may be any of a variety of such electrodes commonly used for control or measurement of the working electrode potential.

Among the other advantages of the electrolytic cell 10 of the present invention, and especially of placing porous anode 28 directly adjacent separator 26, is its ease of construction and its ability to operate effectively even when the conductivity of the solvents being used is quite low. For example, some solvents which can dissolve iodide or iodide sources such as phenyliodide will not dissolve other electrolytes and, therefore, may not impart conductivity. Such a situation may exist where unwanted reactions can occur if salts or water are present. In this situation where the anolyte solution is poorly conductive, the anode 28 can be placed directly adjacent to the separator 26 so that a current can flow and iodination of the protein, peptide or organic molecule can still occur. Since the material to be halogenated is in the anodic half cell 14, a conductive solvent in the cathodic half cell 12 may be used. This construction is shown in FIG. 1. Where anodic solvent conductivity is not a factor with respect to avoiding unwanted chemical reactions between the solvent and the material to be halogenated, however, a conductive solvent may be used and the anode 28 may be placed anywhere within the anodic half cell 14. One efficient means available for placing the anode 28 directly adjacent to the separator 26 is to chemically deposit the anode material onto the separator 26. Example 16 below demonstrates one way of achieving this deposition.

One drawback of using noble metals as the anode materials of the present invention is that they have a high capacity to adsorb iodide and other halogens. For example, it has been found that adsorption of radioiodide onto the anode used for its oxidation to produce the active iodinating species accounts for almost all the inefficiency in the use of the isotope in the electrochemical labeling of antibodies, provided that the technique of using controlled potential or controlled current was properly performed. It is well known that the size of the anode relative to the volume of anolyte determines the time needed for potential-controlled electrolysis, and, hence, the anode cannot always be made smaller without resulting in unreasonably long electrolysis times. Therefore, the problem of loss of activity to adsorption on the anode had to be minimized in some other way.

This problem can be minimized through control of the working electrode surface area/half cell volume ratio (A/V) The inventors have discovered that if the A/V ratio is too small, long electrolysis times are needed, while if it is too large, excessive loss of radiohalide to adsorption occurs. This concern refers specifically to radiohalogenation; other electrochemical conversions or types of radiolabeling reactions may or may not be subject to this difficulty. A general range for the A/V ratio pertaining to the radiohalogenation of proteins is 0.001 to 5000 $cm^{-1}$ and the preferred range is 0.05 to 10 $cm^{-1}$. The geometric area is calculated from the gross physical measurements of the electrode. The parameter that actually determines both the time required for the electrolysis and the capacity to adsorb halogen is the real surface area. The real surface area varies according to the microscopic roughness, which is determined by the form of the electrode (e.g., porous vs. smooth), the history of the electrode, and other factors. The real area may be larger or smaller than the geometric area.

This problem is also minimized in a preferred embodiment of this invention by saturating the anode 28 of the electrolytic cell of the present invention with non-radiohalogen and then minimizing the exchange of radiohalogen with the adsorbed non-radiohalogen during the labeling procedure. Two methods are proposed for saturating the anode 28 with non-radiohalogen: soaking of the porous anode 28 with non-radiohalogen prior to insertion in the electrolytic cell 10; and subjecting the porous anode 28 to electrolysis while located in a solution of non-radiohalogen.

In operation, cell 10 can be operated by controlling the working electrode potential, the cell current, or the overall cell voltage, i.e., the potential across the anode and the cathode). The applied current may be direct or alternating, or the applied potential may be constant or varying according to any given waveform, depending on the requirements of the process of interest. When the potential is controlled, the placement of the reference electrode outside the current path allows the control to be more precise. The proposed reason for this is that this geometry minimizes the contribution of the IR drop (product of cell current times solution resistance) to the potential between the reference and working electrodes. When the cell current or potential is controlled, this geometry provides for more precise measurement of the working electrode potential. In the case of iodinations and radioiodinations in aqueous media, it has been found that for some substrates precise potential control of the anode is essential in order to achieve a high, reproducible yield.

EXAMPLES 1-13: IODINATION OF MONOCLONAL ANTIBODIES

Table A summarizes the Examples 1-13 results of electrolytic radioiodinations of a monoclonal antibody with I-125. The experiments were performed using the electrolytic cell 10 of the present invention to determine the effects varying the amounts of radiolabed halogen and anode pretreatment with the halogen would have on the yield of labeled proteins, peptides and other organic molecles. Because the amount of I-125 used in these experiments was so small compared to the adsorption capcity of the anode 28, solution phase carrier iodide (non-radioactive iodide) was used to obtain the results. A non-radioactive labeling agent, especially a non-radioactive halogen, is one that meets the standards of the U.S. Nuclear Regulatory Commission.

to Table A. Both the cathode 12 and the anode 14 compartments were filled with PBS. If carrier iodide was to be used it was added to the anolyte first, followed by freshly thawed MAb and finally radiochemical I-125. After stirring briefly, the entire anolyte was withdrawn using a 10 ml syringe and counted using a Capintec CRC7 radioisotope calibrator. The anolyte was placed back in the cell, stirring begun, and electrolysis carried out at controlled potential. The potentiostat was a model CVIB cyclic voltammograph, supplied by Bioanalytical Systems, Inc. (BAS-West Lafayette, Ind.). The current was monitored using a digital voltmeter.

The electrolysis was interrupted periodically in order to count the anolyte and to withdraw a 50 microliter sample for HPLC analysis. The sample was diluted with 200 microliter of eluent (400 mM PBS containing sodium azide) and injected onto a gel permeation column. UV (280 nm) and radiation detectors in series provided quantitation of the relative amounts of unbound and MAb-bound I-125.

Following the conclusion of the electrolysis, sometimes the anode 28 was removed from the cell 10 and counted. When this was done, this measurement was used to directly obtain the percentage of the initial I-125 that had become adsorbed on the anode 28. (The anode 28 is the only cell component that was ever found to be significantly radioactive following electrolysis.) The anolyte was always counted, and if the anode 28 was not, the amount adsorbed on the anode 28 was taken to be the difference between the initial count and the final anolyte count. Due to the difficulty of quantitatively

TABLE A

| run # | μCi | nmole carrier | E(mV) | pH | time (min) | anode % | MAb % | unreacted % | notes |
|---|---|---|---|---|---|---|---|---|---|
| 1 | 200 | 100 | 600 | 7.0 | 45 | 7.5 | 77.2 | 15.3 | 1,4,9 |
| 2 | 202 | 0 | 600 | 7.0 | 325 | 95.0 | 0 | 5.0 | 1,4,9 |
| 3 | 232 | 100 | 600 | 7.0 | 192 | 18.4 | 81.6 | 0 | 1,4,9,11 |
| 4 | 231 | 0 | 600 | 7.0 | 32 | 26.8 | 62.2 | 11.0 | 1,5 |
| 5 | 115 | 0 | 650 | 7.0 | 194 | 50.3 | 41.6 | 8.0 | 1,5 |
| 6 | 8710 | 0 | 650 | 7.0 | 121 | 30.8 | 61.1 | 8.2 | 1,5,10,12 |
| 7 | 332 | 3.5 | 650 | 7.0 | 220 | 23.5 | 73.8 | 2.8 | 1,5 |
| 8 | 272 | 0 | 650 | 8.0 | 90 | 32.4 | 58.4 | 9.3 | 1,5 |
| 9 | 306 | 0 | 650 | 7.0 | 180 | 13.7 | 82.9 | 3.4 | 1,6,13 |
| 10 | 240 | 0 | 650 | 7.3 | 106 | 72.9 | 8.4 | 18.7 | 1,7 |
| 11 | 397 | 0 | 650 | 7.3 | 240 | 57.9 | 24.0 | 18.1 | 2,8 |
| 12 | 287 | 7 | 650 | 7.3 | 90 | 18.5 | 72.9 | 8.6 | 2,8 |
| 13 | 310 | 0 | 600 | 7.0 | 30 | 4.5 | 0 | 95.5 | 3 |

Notes on Table A:
E is electrolysis potential in millivolts vs. Ag/AgCl. Anode %, MAb % and unreacted % are the percentages of the initial I-125 bound to the anode, bound to the antibody and left in solution, respectively, at the end of the indicated electrolysis time.
1. anode is Au electroformed mesh, 1000 lines/inch
2. anode is Au electroformed mesh, 670 lines/inch
3. anode is Pt oxide on Pt mesh
4. anode pretreatment: soak in iodide solution at open circuit outside of the radioiodination cell
5. anode pretreatment: electrolysis at 650 mV using 40 or 50 micromolar iodide in the radioiodination cell
6. anode pretreatment: electrolysis at 650 mV using 1 mM iodide in the radioiodination cell
7. anode pretreatment: exposure to 1 mM iodine at open circuit outside of the radioiodination cell
8. anode pretreatment: electrolysis at 650 mV using 1 mM iodide outside the radioiodination cell
9. HPLC evidence of aggregation
10. immunoreactivity = 78.4%
11. carrier iodide was added after the I-125 was already adsorbed on the anode
12. 9 mg MAb
13. 6 mg MAb Before assembly of the cell 10, the separator 26, a cation-exchange membrane, was heated to near boiling in 2 M nitric acid for 2 hours in order to remove impurities. The membrane 26 was then converted to the salt form by soaking in phosphate buffered saline (PBS). The membrane 26 prevented the passage of antibodies from the anolyte to the catholyte. The membrane 26 also ensured that the radioiodide remained in the anoide compartment.

The cell 10 was assembled with an anode 28 pretreated using one of the methods described in the notes removing the anolyte with a syringe, any unaccounted for radioactivity was assumed to be in the residual solution, and the missing quantity was added to the anolyte count.

The first three experiments in Table A were performed using Au anodes that were soaked in iodide outside of the cell in which the radioiodination was to take place. This treatment probably did not produce saturation coverage of adsorbed I, leaving open sites onto which I-125 could adsorb without exchanging with previously adsorbed I. It is hypothesized that when no carrier iodide is used, the I-125 is taken up almost quantitatively by the anode. Use of a large amount of carrier iodide (100 nmole iodide to 33.3 nmole MAb) resulted in very good iodination yields, but showed evidence of aggregation of the monoclonal antibodies. Aggregation is generally known by those skilled in the art to be detrimental to the product in that it changes the biodistribution and pharmacologic activity. Run #3 was begun in a manner similar to run #2 and, after it was verified that the I-125 was taken up by the anode, carrier iodide was added at the indicated level and the electrolysis continued, resulting in the yield shown.

In the next group of experiments (Runs 4–9), the anode was pretreated by oxidizing iodide (no MAb present) in the cell where the radioiodination was to take place, followed by extensive rinsing of the cell (notes 5,6). With this pretreatment, it appeared that no carrier iodide was necessary in order to get good yields. However, separate experiments indicated that it was difficult to completely remove by rinsing all of the iodide and/or iodine from the pretreatment, so these experiments may have had an undetermined level of carrier after all. In any event, there was no evidence of aggregation of the monoclonal antibodies.

In the next group of three experiments in Table A (runs 10, 11 and 12), the anode was pretreated outside of the cell (notes 7 and 8) so that it was certain that the level of carrier was accurately known. With no added carrier, the yield of labeled material was poor, with most of the activity ending up on the anode. However, addition of a modest amount of carrier substantially improved the yield without any evidence of aggregation of the monoclonal antibodies. It appeared from these results that carrier could be added at least up to a level such that the molar ratio of total iodide to monoclonal antibody was approximately 0.2 without damage to the antibody.

Examples 1–13 illustrate that, where the amount of I-125 used was very small compared to the adsorption capacity of the anode 28, the method of anode pretreatment and the level of carrier iodide were very important factors in determining the yield of labeled monoclonal antibody. Yields (based on initial I-125) of labeled MAb in the range of 70–80% were achieved with little or no carrier when the method of anode pretreatment with non-radioiodide was by electrolysis rather than by presoaking the anode.

Example 14 illustrates similar or better yields are obtained without the use of solution-phase carrier when production scale activity levels of I-125 are used.

EXAMPLE 14

The cell of the present invention was used in an improved process for radioiodination of a tumor-specific monoclonal antibody with I-125. This material is useful for the detection of small tumors, for example, or those tumors that may otherwise not be detected, for surgical removal.

The cell was constructed to provide an anolyte volume of 5 ml and a geometric anode surface area of 2.9 $cm^2$ (one side). The membrane used to separate the anode and cathode compartments was a Nafion 117 strong cation exchange membrane. The anode material was gold electroformed mesh, 670 lines $in^{-1}$ that had been pretreated by electrolysis of a 1 mM solution of nonradioactive iodide in order to saturate the iodine adsorption sites. The anode used in the experiment had been used for two prior experiments without repeating the iodide electrolysis but was soaked between experiments with 1 M NaOH followed by careful rinsing with phosphate buffered saline (PBS).

The following procedure was followed for radioiodination: 2 ml of PBS containing 60 mg of antibody, 1 ml of I-125 solution (105 mCi) and sufficient pH 7 PBS to make a total volume of 5 ml added to the anode compartment. The cathode compartment was filled with PBS. The anolyte was stirred magnetically as electrolysis was begun at +0.650 V (vs. a silver/silver chloride reference electrode). Electrolysis was stopped after 90 minutes and the anolyte removed. The anolyte and the cell were counted in order to determine the loss of radioiodide to adsorption at the anode. After electrolysis, 96.4 mCi were present in the anolyte while 8.6 mCi remained in the cell.

Precipitation with trichloroacetic acid showed that 5.0% of the anolyte radioactivity was not covalently bound to the antibody. This result together with the total anolyte count indicated that the total yield of radioiodinated product based on the initial I-125 was 87%. HPLC analysis of the anolyte indicated that >97% of the radiolabeled antibody was in monomeric form. 82.7% of the radiolabeled antibody was immunoreactive.

In addition to being able to achieve the radiohalogenation of monoclonal antibodies, the electrolytic cell of the present invention and the process of its use is capable of achieving the radiohalogenation of other proteins, peptides and organic molecules. The following specific examples are directed to several embodiments of the present invention and are not to be construed as limiting the scope of the invention.

EXAMPLE 15: IODINATION OF TYROSINE AT pH 9.0

The cell was assembled with a Pt gauze cathode, gold electroformed mesh anode (670 lines per inch, geometric area 3.5 $cm^2$) and Nafion 117 cation exchange membrane separator. The catholyte was pH 9.0 buffer (0.20 M potassium phosphate, 0.10 M sodium chloride, adjusted to pH 9.0 with NaOH). The anolyte consisted of 3.0 ml 1.07 mM L-tyrosine (3.07 micromole) in pH 9.0 buffer and 2.0 ml of pH 9.0 buffer. 150 microliters of 10.0 mM NaI solution (1.53 micromole iodide) was added to the anolyte via syringe and electrolysis was carried out at +600 mV vs. Ag/AgCl (3M KCl) The anolyte only was stirred magnetically. After 90 minutes, the electrolysis was terminated and the anolyte analyzed using high pressure liquid chromatography. At 84% iodide conversion, the yield of 3-iodo-L-tyrosine was 72% based on initial iodide.

EXAMPLE 16: CHEMICAL DEPOSITION OF GOLD ANODE ONTO ANION EXCHANGE MEMBRANE PRIOR TO IODINATION OF TYROSINE

Gold was chemically deposited on a Raipore 4030 anion exchange membrane as follows: using a two compartment reactor with the membrane itself as the separator, 0.02 M $AuCl_3$(pH 1) solution was placed on one side and 0.1 M hydrazine solution (pH 13) on the other. After 45 minutes, the metallized membrane was removed from the reactor, rinsed with deionized water, and soaked 10 minutes in a solution of iodine (1 mM) in 70% methanol, 30% water. The metallized membrane was then washed several times with 70% methanol and soaked in several changes of pH 9.0 buffer. Electrolysis using this metallized membrane as the anode and separator was performed in the same cell and followed the same procedure as in Example 15. At 88% iodide conversion, the yield of 3-iodo-L-tyrosine was 40% based on initial iodide (only the anolyte was sampled).

EXAMPLE 17: ADDITION OF IODIDE TO CATHOLYTE PRIOR TO IODINATION OF TYROSINE

When labeling a compound with radioactive iodine, it may be desirable in some cases to minimize the unreacted radioiodide remaining in the product solution following electrolysis without resorting to excessively long electrolysis times. This concept can be demonstrated with non-radioactive iodide by using the present invention in the following manner: the cell was assembled using the metallized membrane described in Example 16. The electrolysis was carried out as in Example 15, with the exceptions that the iodide was added to the catholyte, and both anolyte and catholyte were magnetically stirred. The yield of 3-iodo-L-tyrosine was 45% based on the initial iodide added to the catholyte, and the concentration of iodide in the anolyte was effectively zero.

EXAMPLE 18: IODINATION OF TYROSINE AT pH 7.0

Electrolysis was carried out using the same cell, the pH of the anolyte and catholyte was 7.0. At 85% iodide conversion, the yield of 3-iodo-L-tyrosine was 58% based on initial iodide.

EXAMPLE 19: VAPOR DEPOSITION OF GOLD ANODE ONTO ULTRAFILTRATION MEMBRANE PRIOR TO IODINATION OF TYROSINE

Gold was vapor deposited to a thickness of 150 angstroms on polysulfone ultrafiltration membrane (molecular weight cutoff 100,000). This metallized membrane assembly was used for iodination of L-tyrosine using the same procedure as in Example 18. At 45% iodide conversion, the yield of 3-iodo-L-tyrosine was 54% based on initial iodide (100% iodination selectivity within experimental error).

EXAMPLE 20: IODINATION OF NON-STEROIDAL ESTROGEN

The cell was used to effect the following iododestannylation reaction:

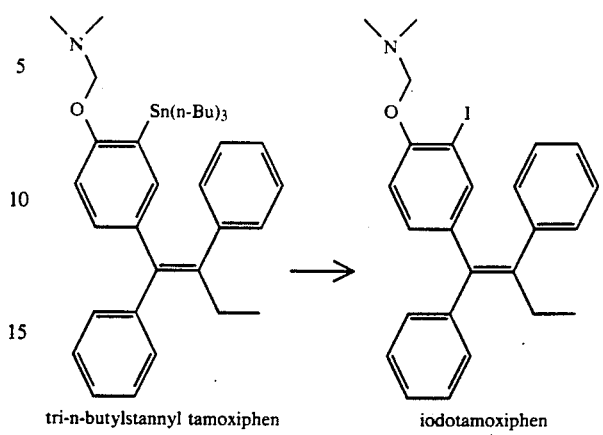

tri-n-butylstannyl tamoxiphen → iodotamoxiphen

Tamoxiphen is a non-steroidal estrogen analog with affinity for the estrogen receptor and with antiestrogenic activity in vivo. The radiolabeled iodo derivative is potentially useful as a gamma-ray emitting tracer for the receptor Iodotamoxiphen is prepared in this example using non-radioactive iodide in order to demonstrate the applicability of the invention.

The cell was assembled with a Pt/Rh gauze anode (10% Rh, 80 mesh), Pt gauze cathode and Nafion 117 cation exchange membrane separator. The catholyte was aqueous pH 7.0 buffer. The anolyte consisted of approximately 5 ml of methanol containing 0.086 g tri-n-butylstannyl tamoxiphen (0.00013 mole) and 0.042 g NaI (0.00028 mole). No other supporting electrolyte was added to the anolyte. Electrolysis was carried out with magnetic stirring of the anolyte for approximately 2.5 hr. at +500 mV vs Ag/AgCl (3M KCl). At this time thin layer chromatography of the anolyte (silica gel, eluent 5% methanol in chloroform) indicated complete conversion of tri-n-butylstannyl tamoxiphen. The anolyte was removed from the cell, diluted with 30 ml diethyl ether, and washed with 10 ml of 10% sodium metabisulfite and two 10 ml portions of 1M NaOH. The organic phase was separated, dried over anhydrous magnesium sulfate, and filtered. The solvent was evaporated under a gentle stream of dry nitrogen, leaving 0.051 g (0.00010 mole) of colorless oil. The $^1$H and $^{13}$C NMR spectra of this product (in CDCl$_3$) were consistent with the desired compound iodotamoxiphen.

EXAMPLE 21: IODINATION OF 17-ALPHA-(TRIBUTYLSTANNYL)-VINYLESTRADIOL

Radiolabeled derivatives of 17-alpha-iodovinylestradiol are also useful as gamma-emitting pharmaceuticals that bind selectively to estrogen receptor sites. This example demonstrates the utility of the cell for synthesis of 17-alpha-iodovinylestradiol via iododestannylation of 17-alpha-(tributylstannyl) vinylestradiol:

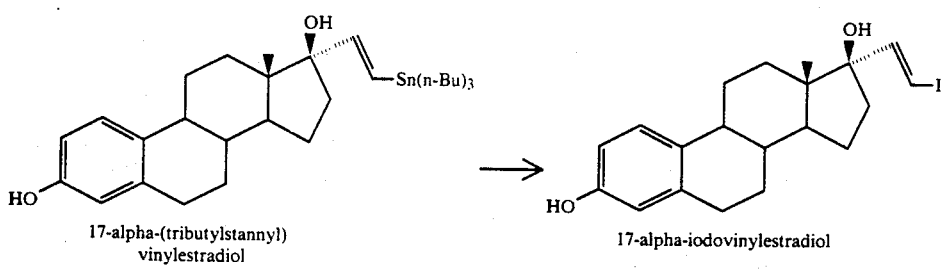

The cell was assembled with a gold electroformed mesh anode (geometric area 3.9 cm²), 304 stainless steel gauze cathode (40 mesh) and Nafion 117 cation exchange membrane separator. The catholyte consisted of pH 7.0 buffer. The anolyte consisted of 5 ml of 10% water in methanol to which was added 0.060 g 17-alpha-(tributylstannyl)vinylestradiol (0.00010 mole) and 0.031 g sodium iodide (0.00010 mole). Electrolysis was carried out at +600 mV (vs Ag/AgCl, 3M KCl) with magnetic stirring until thin layer chromatography (silica gel, eluent 20% ethyl acetate in hexane) indicated complete conversion of the 17-alpha-(tributylstannyl)-vinylestradiol. The anolyte was diluted with 20 ml of chloroform and extracted once with aqueous 10% sodium metabisulfite/1% potassium fluoride. The aqueous phase was extracted once with 10 ml of fresh chloroform. The chloroform extracts were combined, dried over anhydrous magnesium sulfate and filtered. The solvent was evaporated under a stream of dry nitrogen, leaving 0.056 g of white solid. This material was dissolved in solvent and purified by flash chromatography using 12 g of 40 micron silica gel and 25% ethyl acetate/hexane eluent. The homogeneous fractions were combined, and evaporation of the solvent gave 0.030 g (0.000071 mole) of white solid. The ¹H and ¹³C NMR spectra, fast atom bombardment mass spectrum and chemical ionization mass spectrum were all consistent with the structure of the desired product 17-alpha-iodovinylestradiol.

EXAMPLE 22: BROMINATION OF ESTRONE ENOLDIACETATE 16-alpha-[⁷⁷Br]bromoestradiol has potential utility for imaging of human breast tumors that contain estrogen receptors. This example demonstrates a synthesis of the non-radioactive analog of this compound from estrone in which the cell is applied to the bromination of an intermediate, estrone enoldiacetate.

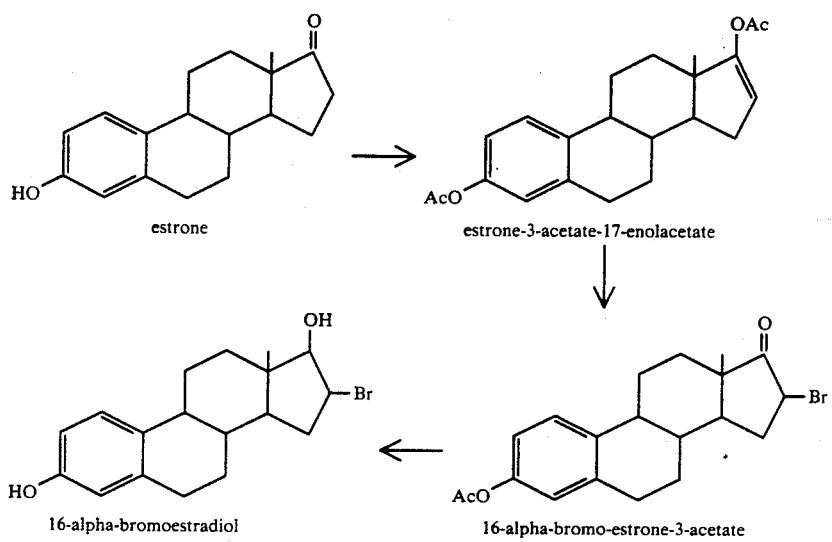

15 ml isopropenyl acetate, 2.0 g estrone (0.0074 mole) and 0.6 ml catalyst solution (0.1 ml concentrated sulfuric acid in 5 ml isopropenyl acetate) were refluxed 2.5 hr. Approximately 4 ml of solvent was then distilled over a period of 1.5 hr. 10 ml of isopropenyl acetate containing 0.5 ml catalyst solution was added and the mixture was slowly distilled to remove about one-half the volume. The remaining mixture was chilled in an ice bath, diluted with 50 ml of anhydrous diethyl ether, and washed with 10 ml saturated aqueous sodium bicarbonate. The organic phase was dried over anhydrous magnesium sulfate, filtered and evaporated to dryness. The residue was dissolved in 1 liter of 20% ethyl acetate in hexane and passed through a short column (5 cm long by 2 cm diameter) of 80–200 mesh neutral alumina. The solution was then evaporated under reduced pressure to a volume of about 50 ml and set aside to allow crystallization of the product, yielding 1.56 g of white crystals (melting range 149°–150° C., literature 149°–150° C.). ¹H and ¹³C NMR spectra were consistent with the desired enol diacetate (estrone-3-acetate-17-enolacetate).

The cell was assembled with a Pt/Rh gauze anode (80 mesh, 3.9 cm² geometric area), a 304 stainless steel cathode (40 mesh) and Nafion 117 cation exchange membrane separator. An electrolyte solution consisting of 10 ml tetrahydrofuran, 7 ml diethyl ether and 33 ml buffer (2.81 g potassium acetate in 50 ml 85% acetic acid, 15% water) was used for the anolyte and the catholyte. The anolyte was 5 ml of electrolyte containing 0.039 g estrone-3-acetate-17-enolacetate (0.00011 mole) and 0.013 g sodium bromide (0.00013 mole). Electrolysis was carried out at +1200 mV (Ag/AgCl, 3M KCl) with magnetic stirring of the anolyte until thin layer chromatography (silica gel, eluent 20% ethyl acetate in hexane) showed complete conversion of estrone-3-acetate-17-enolacetate. The anolyte was added to 25 ml water and the mixture was extracted three times with 10 ml portion of diethyl ether. The ether extracts were combined, dried over anhydrous magnesium sulfate, and filtered. The solvent was removed under a stream of dry nitrogen, leaving behind 0.032 g (0.000082 mole) of white solid. $^1$H and $^{13}$C NMR spectra of the product were consistent with 16-alpha-bromo-estrone-3-acetate.

0.064 g 16-alpha-bromo-estrone-3-acetate (0.00016 mole) was dissolved in 5 ml tetrahydrofuran (THF) and chilled to $-78°$ C. under nitrogen in an isopropanol/dry ice bath. 2 ml of 1.0 M lithium aluminum hydride in THF was added slowly with rapid magnetic stirring. After stirring for 10 minutes, the mixture was quenched by adding 4 ml of 1:1 ethyl acetate in THF (prechilled to $-78°$ C.). The mixture was stirred 5 minutes, then the isopropanol/dry ice bath was replaced by an ice bath. 10 ml of chilled 3 M aqueous HCl was slowly added to finish quenching. 10 more ml of 3 M HCl was added and the mixture was allowed to warm to room temperature. The mixture was extracted three times with 10 ml portions of diethyl ether. The ether extracts were combined, dried over anhydrous magnesium sulfate, and filtered. Evaporation of the solvent under a stream of dry nitrogen yielded 0.075 g of a slightly greenish residue. Thin layer chromatography (silica gel, eluent 25% ethyl acetate in hexane) of this residue indicated at least five components. The mixture was subjected to flash chromatography (15 g 40 mesh silica gel, eluent 25% ethyl acetate in hexane). Combination of homogeneous fractions followed by evaporation of the solvent yielded 0.024 g white solid (the major component, $R_f = 0.31$). The $^1$H and $^{13}$C NMR spectra of this product were consistent with 16-alpha-bromoestradiol. The carbon-13 NMR data suggest that the stereochemistry at position 17 is alpha.

EXAMPLE 23: RADIOIODINATION OF MONOCLONAL ANTIBODY B72.3

The cell was assembled with a gold electroformed mesh anode (670 lines/in, pretreated by soaking in 1 mM non-radioactive iodine), 304 stainless steel mesh cathode and Nafion 117 cation exchange membrane separator. 3 ml of pH 7 PBS was placed in the catholyte chamber. 3 ml of pH 8.1 PBS containing 15 mg of antibody, 1.44 mCi of I-125 and 22 nmole carrier iodide (total iodide equivalent to 40 mCi I-125) was added to the anolyte chamber. With magnetic stirring, electrolysis was carried out at +800 mV (Ag/AgCl, 3 M Cl−). An intermediate sample taken at 30 minutes indicated an iodination yield of 71.8%. After 90 minutes, 9.5% of the initial I-125 was adsorbed on the anode, while 4.5% remained in solution and not bound to the antibody, resulting in an iodination yield of 86.0%.

EXAMPLE 24: RADIOIODINATION OF MONOCLONAL ANTIBODY B72.3

The radioiodination performed in Example 23 was repeated except that the anode potential was set at +850 mV while using the same reference electrode. A sample at 30 minutes indicated an iodination yield of only 31.8%.

Examples 15 through 24 illustrate additional uses of the electrolytic cell of the present invention. Examples 15 and 18 illustrate the effect that pH has on the iodination of L-tyrosine. Examples 16 and 17, on the other hand, compare the addition of iodide to the anolyte with the addition to the catholyte using a cell with an anion exchange membrane in each experiment. The advantage of adding the iodide to the catholyte is the minimization of unreacted iodide in the product solution. Example 16, 17 and 19 are also examples of where the separator 26 serves as a solid support for the deposition of the anodic material to allow the anode 28 to be adjacent the separator 26. Finally, Examples 20, 21, 22, 23 and 24 illustrate the halogenation of other organic molecules.

In the above examples ambient temperature was chosen for convenience, but lower or higher temperatures may be used, the primary concern being stability of the material to be labeled. The pH, and concentration and nature of buffer constituents may also vary over wide ranges, the primary consideration again being the stability of the material to be labeled. The potential of the working electrode, the ratio of the working electrode area to working cell volume and the presence of the reference electrode are the means by which the maximum rate of labeling can be achieved while minimizing oxidative damage to the protein.

The foregoing detailed description is given for clearness of understanding only and no unnecessary limitations should be understood therefrom, as modifications within the scope of the invention will be apparent to those skilled in the art.

We claim:

1. A process for labeling proteins, peptides and other organic molecules which comprises:
   (a) providing an electrolytic cell having a cathodic half cell and an anodic half cell divided by a separator; providing a porous working electrode in one of said cathodic half cell and said anodic half cell; providing a counter electrode in the other of said cathodic half cell and said anodic half cell; and providing a reference electrode located in said loaf cell containing said working electrode and outside the current path between said porous working electrode and said counter electrode;
   (b) inserting the to be labeled into said half cell containing said working electrode;
   (c) contacting said material to be labeled with a labeling agent; and
   (d) passing a current through said electrolytic cell.

2. A process in accordance with claim 1, which includes positioning said porous working electrode directly adjacent said separator.

3. A process in accordance with claim 2, which includes providing an anion exchange membrane to serve as said separator.

4. A process in accordance with claim 3, wherein said contacting step comprises the step of adding said labeling agent to said half cell containing said counter electrode and allowing it to migrate through said anion exchange membrane to said porous working electrode for reaction with said material to be labeled.

5. A process in accordance with claim 4, in which said step of providing a porous working electrode includes depositing a working electrode material on said separator.

6. A process in accordance with claim 2, which includes providing a cation exchange membrane to serve as said separator.

7. A process in accordance with claim 1, which includes making said porous working electrode from a metal selected from the group consisting of gold, platinum and a mixture of 90% platinum/10% rhodium.

8. A process in accordance with claim 1, which includes making said counter electrode from a metal selected from the group consisting of stainless steel and platinum.

9. A process in accordance with claim 1, which includes providing an anion exchange membrane to serve as said separator.

10. A process in accordance with claim 1, which includes providing a cation exchange membrane to serve as said separator.

11. A process in accordance with claim 1, wherein said step of passing current comprises the step of controlling the working electrode potential with said reference electrode.

12. A process in accordance with claim 11, wherein said contacting step comprises the step of adding said labeling agent to said half cell containing said working electrode.

13. A process in accordance with claim 11, wherein said contacting step comprises the step of adding said labeling agent to said half cell containing said counter electrode and allowing it to migrate through said separator to said porous working electrode for reaction with the material to be labeled.

14. A process in accordance with claim 1, in which said step of providing a porous working electrode includes depositing a working electrode material on said separator.

15. A process in accordance with claim 1, in which the labeling agent is a radioactive labeling agent.

16. A process in accordance with claim 15, in which the radioactive labeling agent is a radioactive halide.

17. A process in accordance with claim 12, in which the radioactive halide is I-125.

18. A process in accordance with claim 15, whrien the ratio of the surface area of said working electrode of the volume of said half cell containing said working electrode is from about 0.001 to about 5000 $cm^{-1}$.

19. A process in accordance with claim 18, wherein the ratio of the surface area of said working electrode to the volume of said half cell containing said working electrode is from about 0.05 to about 10 $cm^{-1}$.

20. A process in accordance with claim 1, wherein the ratio of the surface area of said working electrode to the volume of said half cell containing said working electrode is from about 0.001 to about 5000 $cm^{-1}$.

21. A process in accordance with claim 20, wherein the ratio of the surface area of said working electrode to the volume of said half cell containing said working electrode is from about 0.05 to about 10 $cm^{-1}$.

* * * * *